(12) United States Patent
Park

(10) Patent No.: US 10,792,021 B2
(45) Date of Patent: Oct. 6, 2020

(54) BIOPSY DEVICE AND SYSTEM

(71) Applicant: Hee Boong Park, Seoul (KR)

(72) Inventor: Hee Boong Park, Seoul (KR)

( * ) Notice: Subject to any disclaimer, the term of this patent is extended or adjusted under 35 U.S.C. 154(b) by 37 days.

(21) Appl. No.: 15/303,450

(22) PCT Filed: Apr. 10, 2015

(86) PCT No.: PCT/KR2015/003621
§ 371 (c)(1),
(2) Date: Oct. 11, 2016

(87) PCT Pub. No.: WO2015/156639
PCT Pub. Date: Oct. 15, 2015

(65) Prior Publication Data
US 2017/0035398 A1    Feb. 9, 2017

(30) Foreign Application Priority Data

Apr. 10, 2014  (KR) .................... 10-2014-0043035

(51) Int. Cl.
*A61B 10/02*  (2006.01)

(52) U.S. Cl.
CPC ...... *A61B 10/0275* (2013.01); *A61B 10/0283* (2013.01); *A61B 2010/0208* (2013.01); *A61B 2010/0225* (2013.01)

(58) Field of Classification Search
None
See application file for complete search history.

(56) References Cited

U.S. PATENT DOCUMENTS

| | | |
|---|---|---|
| 5,526,822 A | 6/1996 | Burbank et al. |
| 5,775,333 A | 7/1998 | Burbank et al. |
| 6,086,544 A | 7/2000 | Hibner et al. |
| 6,485,436 B1 | 11/2002 | Truckai et al. |
| 7,419,472 B2 | 9/2008 | Hibner et al. |
| 8,177,728 B2 | 5/2012 | Hibner et al. |

(Continued)

FOREIGN PATENT DOCUMENTS

| | | |
|---|---|---|
| CN | 100566665 C | 12/2009 |
| JP | P2006-239433 A | 9/2006 |

(Continued)

*Primary Examiner* — Patrick Fernandes
*Assistant Examiner* — Benjamin S Melhus
(74) *Attorney, Agent, or Firm* — Novick, Kim & Lee, PLLC; Jae Youn Kim

(57) ABSTRACT

Provided are a biopsy device and system for effectively collecting tissue samples by cutting human tissue. The biopsy device of the present invention consists of a needle, a cutter, a drive mechanism, a vacuum line and an air inlet line. The biopsy system of the present invention comprises: a vacuum source connected to the vacuum line; and a solenoid actuator for closing and opening the passageway by pressing and releasing a flexible tube of the air inlet line. The present invention creates the atmospheric pressure at the rear end of the transporting direction of a tissue sample while creating a low pressure at the front end of the transporting direction of the tissue sample by suction of the vacuum source, thereby generating a pressure difference between the front end and the rear end of the transporting direction of the tissue sample, and thus has an effect of smoothly transporting tissue samples.

3 Claims, 14 Drawing Sheets

(56) References Cited

U.S. PATENT DOCUMENTS

| | | | |
|---|---|---|---|
| 8,206,316 B2 | 6/2012 | Hibner et al. | |
| 2006/0074343 A1* | 4/2006 | Hibner | A61B 10/0275 600/566 |
| 2010/0152610 A1* | 6/2010 | Parihar | A61B 10/0275 600/566 |
| 2010/0185150 A1* | 7/2010 | Zacharias | A61M 1/0031 604/119 |
| 2010/0317998 A1* | 12/2010 | Hibner | A61B 10/0275 600/567 |
| 2012/0232495 A1* | 9/2012 | Coon | A61M 39/281 604/250 |
| 2014/0020687 A1* | 1/2014 | Cullen | A61M 16/0066 128/204.23 |

FOREIGN PATENT DOCUMENTS

| | | |
|---|---|---|
| JP | P2008-200481 A | 9/2008 |
| KR | 10-0213463 B1 | 8/1999 |
| KR | 10-2005-0032018 A | 4/2005 |
| KR | 10-2006-0123385 A | 12/2006 |
| KR | 10-2010-0133903 A | 12/2010 |
| KR | 10-2013-0126574 A | 11/2013 |
| KR | 10-2014-0033876 A | 3/2014 |

* cited by examiner

BIOPSY DEVICE AND SYSTEM

TECHNICAL FIELD

The present invention relates to a biopsy device and system and, more specifically, to a biopsy device and system for effectively collecting tissue samples by cutting human body tissue.

BACKGROUND ART

A biopsy is one of histopathological examinations which perform diagnosis by collecting a sample of a living body cell, tissue or the like of a lesion area of a patient and analyzing the sample. The biopsy is mainly performed in the case where a disease such as a cancer or the like is suspected. The biopsy is classified into an excisional biopsy, an incisional biopsy, a percutaneous biopsy, and so forth.

Techniques relating to a biopsy device and system are disclosed in many patent documents such as U.S. Pat. No. 5,526,822 entitled "Method and apparatus for automated biopsy and collection of soft tissue", U.S. Pat. No. 5,775,333 entitled "Apparatus for automated biopsy and collection of soft tissue", U.S. Pat. No. 6,086,544 entitled "Control apparatus for an automated surgical biopsy device", U.S. Pat. No. 6,485,436 entitled "Pressure-assisted biopsy needle apparatus and technique", U.S. Pat. No. 7,419,472 entitled "Biopsy instrument with internal specimen collection mechanism", U.S. Pat. No. 8,177,728 entitled "Valve mechanism for tetherless biopsy device", and U.S. Pat. No. 8,206,316 entitled "Tetherless biopsy device with reusable portion". The disclosure of the above-cited patent documents is incorporated herein by reference.

A biopsy device of some patent documents includes a housing, a needle, a cutter, a cutter driver and a vacuum chamber. The needle extends from the housing and includes a passageway, a tissue receiving port or an opening. The cutter is disposed within the passageway of the needle so that the cutter can make rotation and translational movement in order to cut tissue. The cutter includes a passageway communicating with the passageway of the needle. The vacuum chamber is connected to the passageway of the needle. In order to collect a cut tissue sample, the vacuum chamber is configured to transport the tissue sample from the tissue receiving port along the passageways of the needle and the cutter and discharge the tissue sample to the outside of the cutter. The tissue sample discharged to the outside of the cutter is collected in a tray or a cartridge. The vacuum chamber or the vacuum source is provided with a vacuum pump for generating an air suction force.

However, the biopsy device of the related art described above has a problem in that, when the tissue sample is transported along the passageways of the needle and the cutter by generating a vacuum pressure through the operation of the vacuum pump, a low pressure acts at a transport-direction rear end of the tissue sample, thereby preventing smooth transport of the tissue sample. If the passageways of the needle and the cutter are clogged with the tissue sample, a tissue sample needs to be collected again through the use of a new biopsy device.

In an effort to smoothly collect a tissue sample, U.S. Pat. No. 7,419,472 discloses a flexible push rod disposed so that the flexible push rod can make translational movement along passageways of a needle and a cutter. The push rod is configured to push a transport-direction rear end of a tissue sample when transporting the tissue sample, thereby assisting the transport of the tissue sample. However, a drive mechanism for mechanically operating the push rod, which is composed of a worm gear, a drive block and the like, suffers from a problem of a complex configuration, a complicated assembly process and an increased manufacturing cost.

U.S. Pat. No. 6,485,436 discloses a pressurization source connected to an inflow passageway or channel communicating with a sample receiving port. The pressurization source assists the transport of a tissue sample by delivering a high pressure flow of a gas or liquid suitable for a living body to the sample receiving port through the inflow passageway or channel when transporting the tissue sample. However, the use of the expensive pressurization source for delivering a high pressure flow of a gas or liquid and the use of components such as a fitting and the like for interconnecting the pressurization source and the inflow passageway or channel pose a problem of a high manufacturing cost.

SUMMARY OF THE INVENTION

In view of the various problems inherent in the biopsy device of the related art mentioned above, it is an object of the present invention to provide a novel biopsy device and system capable of generating a pressure difference between a transport-direction front end and a transport-direction rear end of a tissue sample in order to transport the tissue sample.

Another object of the present invention is to provide a biopsy device and system capable of smoothly performing the transport of a tissue sample by creating a low pressure at a transport-direction front end of the tissue sample and creating an atmospheric pressure at a transport-direction rear end of the tissue sample through the suction of a vacuum source.

A further object of the present invention is to provide a biopsy device and system capable of creating an atmospheric pressure at a transport-direction rear end of a tissue sample through the use of simple configurations and inexpensive components such as a flexible hose and a solenoid actuator, thereby saving a manufacturing cost.

A still further object of the present invention is to provide a biopsy device and system capable of improving the ease of assembly and saving a manufacturing cost through the use of a simple structure in which the drive power of an electric motor for causing a cutter to make rotation and translational movement is delivered by a single gear train.

According to one aspect of the present invention, there is provided a biopsy device for cutting tissue and collecting a tissue sample, including: a needle including a proximal end blocked by a tip, a distal end, a passageway and a sample receiving port configured to introduce the tissue and formed on an outer surface of the needle neighboring the distal end so as to communicate with the passageway; a cutter disposed in the passageway of the needle so as to make rotation and translational movement, the cutter including s proximal end disposed within the passageway of the needle, a distal end disposed outside the passageway of the needle and a passageway communicating with the passageway of the needle; a drive mechanism configured to cause the cutter to make rotation and translational movement; a vacuum line configured to suck the tissue and the tissue sample and connected to the passageway of the cutter; and an air inflow line configured to interconnect the passageway of the needle and the atmosphere existing outside the needle so as to create an atmospheric pressure within the passageway of the needle neighboring a transport-direction rear end of the tissue sample when sucking the tissue sample.

Furthermore, the air inflow line includes: a flexible tube including a passageway connected to the passageway of the needle; and a solenoid actuator configured to selectively press and release the flexible tube so as to open and close a passageway of the flexible tube. The solenoid actuator is configured to create an atmospheric pressure within the passageway of the needle by releasing the flexible tube and opening the passageway of the needle before the sample receiving port is closed by the cutter.

According to another aspect of the present invention, there is provided a biopsy system for cutting tissue and collecting a tissue sample, including: a needle including a proximal end blocked by a tip, a distal end, a passageway and a sample receiving port configured to introduce the tissue and formed on an outer surface of the needle neighboring the distal end so as to communicate with the passageway; a cutter disposed in the passageway of the needle so as to make rotation and translational movement, the cutter including s proximal end disposed within the passageway of the needle, a distal end disposed outside the passageway of the needle and a passageway communicating with the passageway of the needle; a drive mechanism configured to cause the cutter to make rotation and translational movement; a vacuum source connected to the passageway of the cutter by a vacuum line so as to suck the tissue and the tissue sample; an air inflow line including a flexible tube configured to interconnect the passageway of the needle and the atmosphere existing outside the needle so as to create an atmospheric pressure within the passageway of the needle neighboring a transport-direction rear end of the tissue sample when sucking the tissue sample; and a solenoid actuator configured to selectively press and release the flexible tube so as to open and close a passageway of the flexible tube.

The biopsy device and system according to the present invention has an effect capable of smoothly transporting a tissue sample by generating a pressure difference between a transport-direction front end and a transport-direction rear end of the tissue sample by creating a low pressure at the transport-direction front end of the tissue sample and creating an atmospheric pressure at the transport-direction rear end of the tissue sample through the suction of a vacuum source. Furthermore, the biopsy device and system according to the present invention has an effect capable of creating an atmospheric pressure at a transport-direction rear end of a tissue sample through the use of simple configurations and inexpensive components such as a flexible hose exposed to the atmosphere and a solenoid actuator for pressing or releasing the flexible hose so as to open or close a passageway of the flexible hose, thereby saving a manufacturing cost. Moreover, the biopsy device and system according to the present invention has an effect capable of improving the ease of assembly and saving a manufacturing cost through the use of a simple structure in which the drive power of an electric motor for causing a cutter to make rotation and translational movement is delivered by a single gear train.

MODE FOR CARRYING OUT THE INVENTION

Other objects, specific advantages and novel features of the present invention will become more apparent from the following detailed descriptions of preferred embodiments made in conjunction with the accompanying drawings.

Preferred embodiments of a biopsy device and system according to the present invention will now be described in detail with reference to the accompanying drawings.

Figure 1:
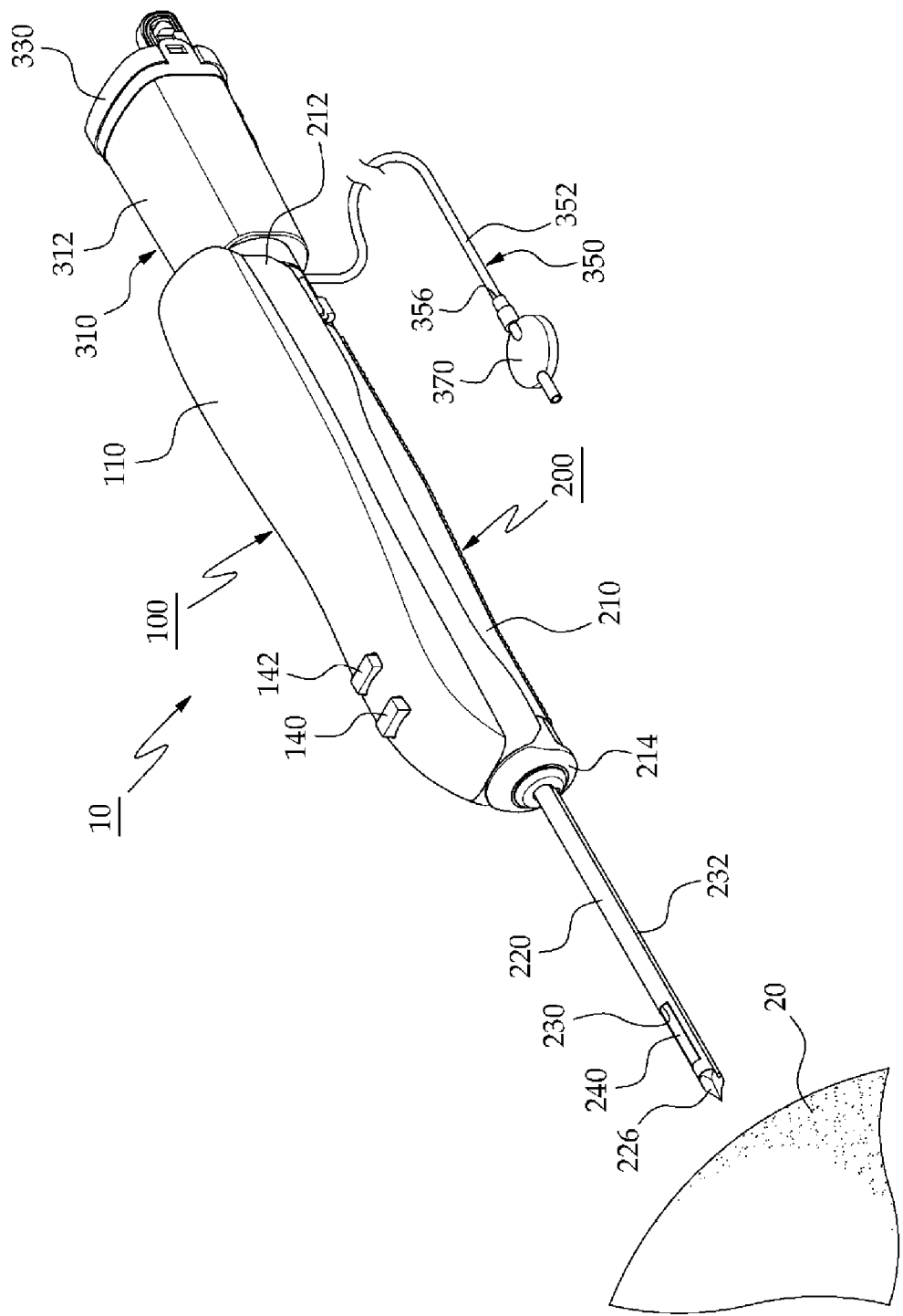
FIG. 1 is a perspective view illustrating the configuration of a biopsy device according to the present invention, in which a drive unit and a probe unit are coupled to each other.
Figure 2:
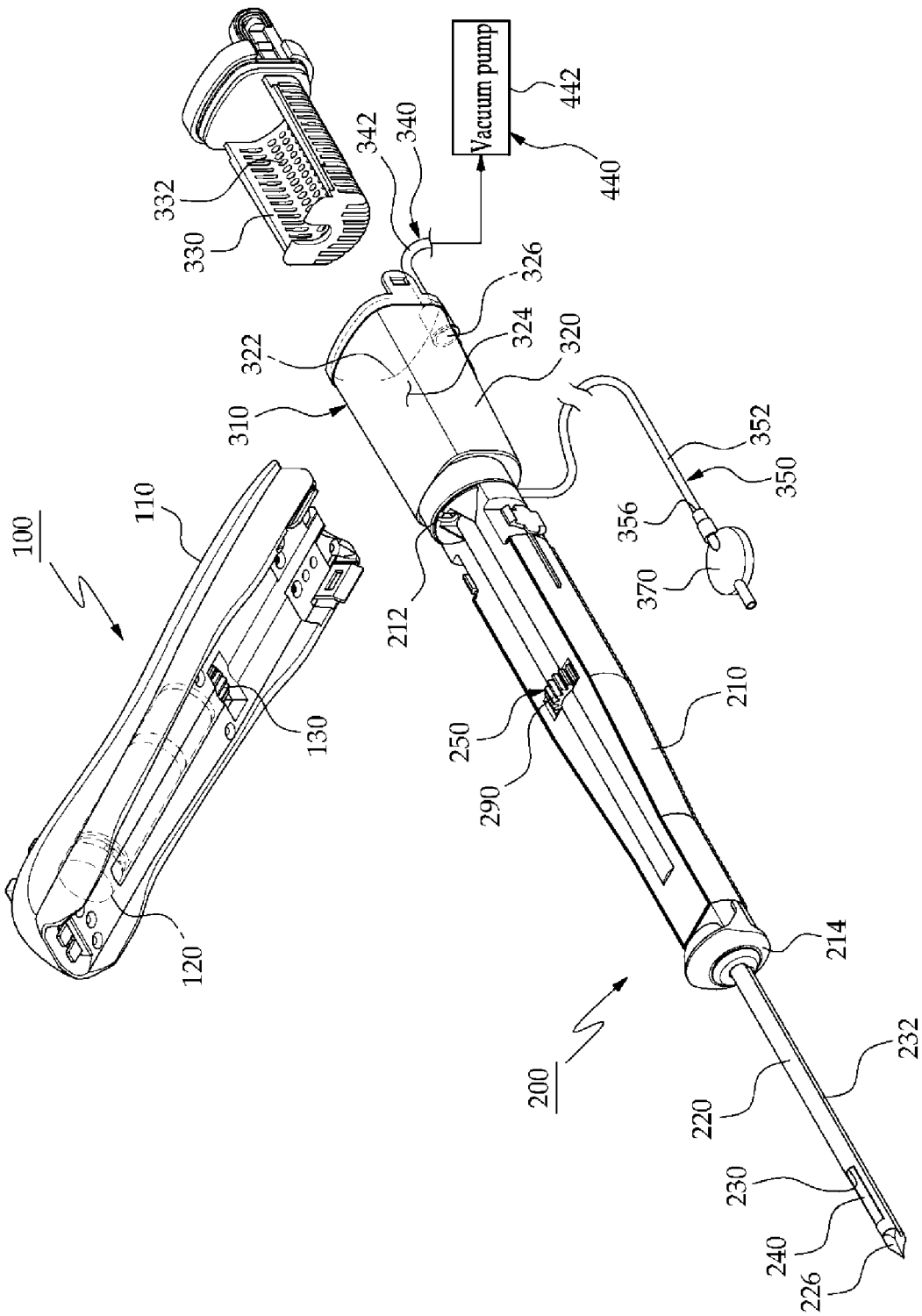
FIG. 2 is a perspective view illustrating the configuration of a biopsy system according to the present invention, in which the drive unit and the probe unit are separated from each other.

Referring first to FIGS. 1 and 2, the biopsy system 10 according to the present invention includes a drive unit 100 and a probe unit 200, both of which constitute a biopsy device. The drive unit 100 and the probe unit 200 are combined in a pair and are used in collecting a sample of tissue 20. The drive unit 100 and the probe unit 200 are configured so that they can be held and used by one hand of a user. After collecting a tissue sample, the probe unit 200 is separated from the drive unit 100 and is discarded. The drive unit 100 is combined with a new probe unit and is reused.

The drive unit 100 includes a drive housing 110, an electric motor 120, a driving gear 130, an aperture button 140 and a cutting button 142. The electric motor 120 is mounted inside the drive housing 110. The driving gear 130 is connected to a shaft 122 of the electric motor 120 so that the driving gear 130 can be rotationally driven by the electric motor 120. The lower portion of the driving gear 130 protrudes from the lower surface of the drive housing 110. The aperture button 140 and the cutting button 142 are respectively mounted to the front region of the upper surface of the drive housing 110. A user may adjust the collection amount of a tissue sample by operating the aperture button 140. A user may perform the cutting of tissue by operating the cutting button 142.

Figure 6:
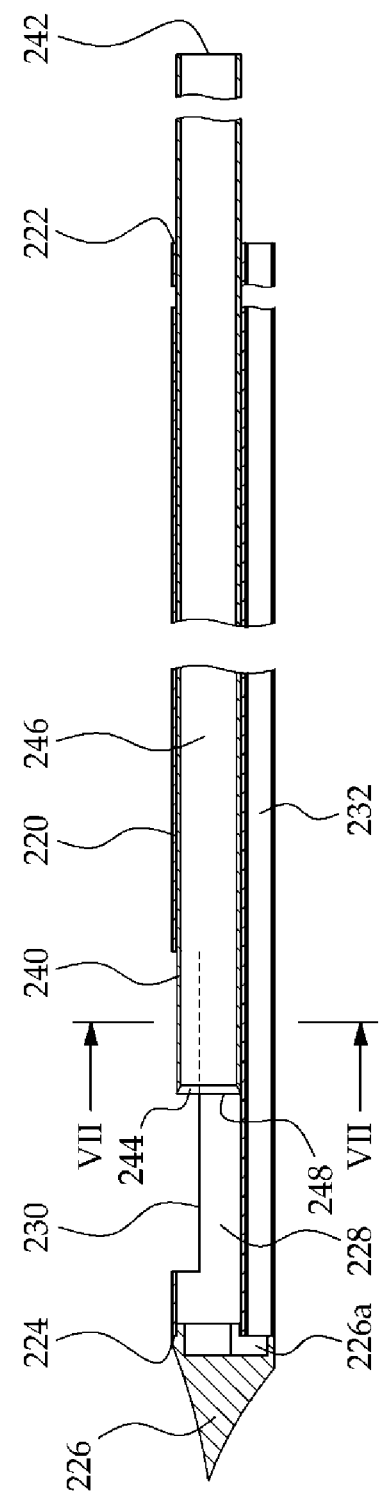
FIG. 6 is a sectional view illustrating the configurations of the needle and the cutter of the biopsy system according to the present invention.
Figure 7:
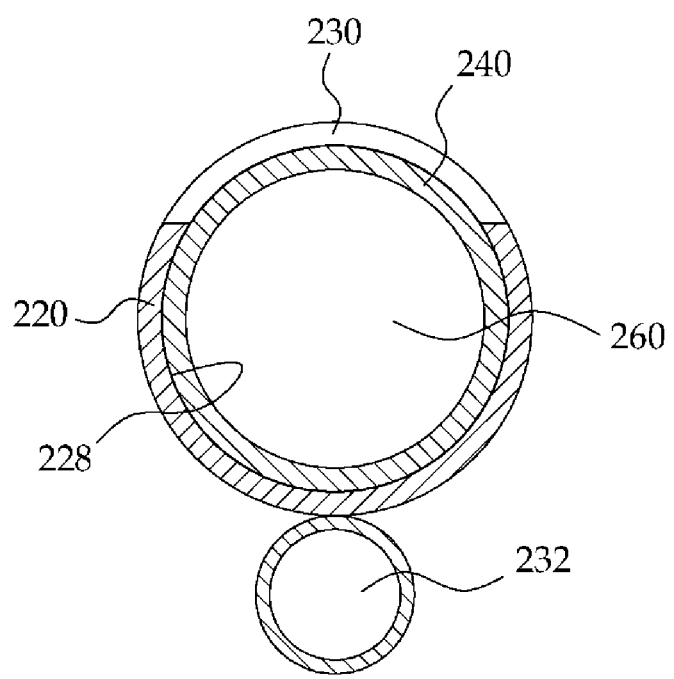
FIG. 7 is an enlarged sectional view taken along line VII-VII in FIG. 6.
Figure 8:
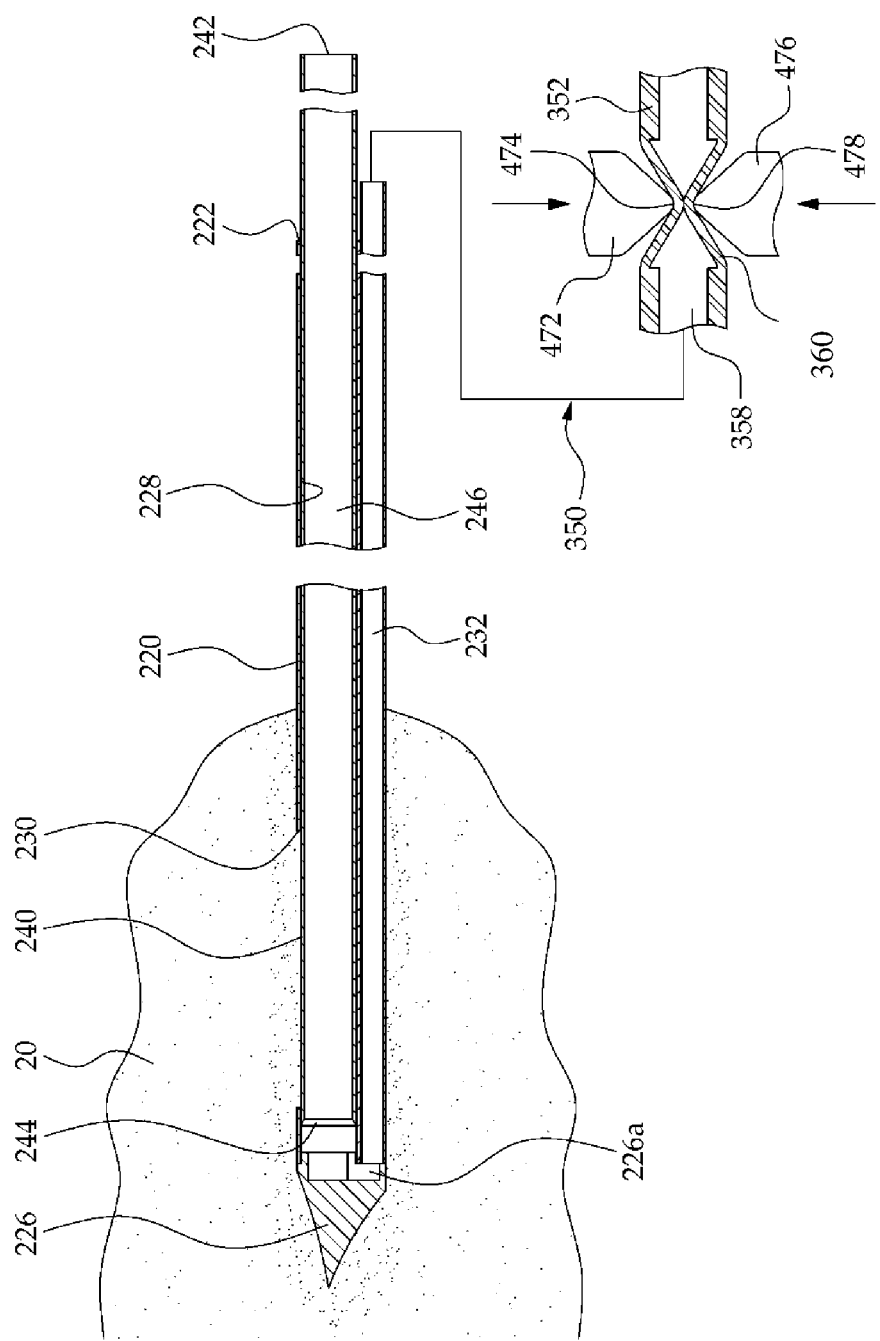
FIG. 8 is a sectional view illustrating an operation of sticking the needle into tissue in the biopsy system according to the present invention.

Referring to FIGS. 1 to 7, the probe unit 200 includes a probe housing 210 and a needle 220. The probe housing 210 is configured so that it can be coupled to and separated from the drive housing 110. The probe housing 210 includes a proximal end 212 and a distal end 214. The needle 220 is formed of an elongated hollow tube and includes a proximal end 222, a distal end 224, a tip 226, a passageway 228, a sample receiving port 230 and an air inflow passageway 232. The proximal end 222 is opened and is coupled to the distal end 212 of the probe housing 210. The distal end 224 extends along the longitudinal direction of the probe housing 210 and is blocked by the tip 226. The passageway 228 is formed inside the needle 220 so as to interconnect the proximal end 222 and the distal end 224. The sample receiving port 230 is formed on an upper outer surface of the needle 220, which neighbors the distal end 224, so as to communicate with the passageway 228. The air inflow passageway 232 is formed in a lower region of an outer surface of the needle 220 along the longitudinal direction of the needle 220 so as to be partitioned from the passageway 228. The air inflow passageway 232 communicates with the passageway 228 at the distal end 224. The passageway 228 and the air inflow passageway 232 are connected by a connection passageway 226a formed on an inner surface of the tip 226. As illustrated in FIGS. 6 and 7, the air inflow passageway 232 is configured by welding an elongated hollow tube to the lower region of the outer surface of the needle 220.

The probe unit 200 includes a cutter 240 disposed within the passageway 228 of the needle 220 so that the cutter 240 can make rotation and translational movement in order to cut tissue 20. The cutter 240 is formed of an elongated hollow tube and includes a proximal end 242, a distal end 244, a passageway 246 and a blade edge 248. The proximal end 242 is opened and is disposed within the probe housing 210 by protruding away from the proximal end 222 of the needle 220. The distal end 244 is inserted into the passageway 228 of the needle 220. The passageway 246 is formed so as to interconnect the proximal end 242 and the distal end 244 of the cutter 240 and is coaxially disposed so as to communicate with the passageway 228 of the needle 220. The blade edge 248 is formed at the distal end 244 in order to cut the tissue 20.

Figure 3:
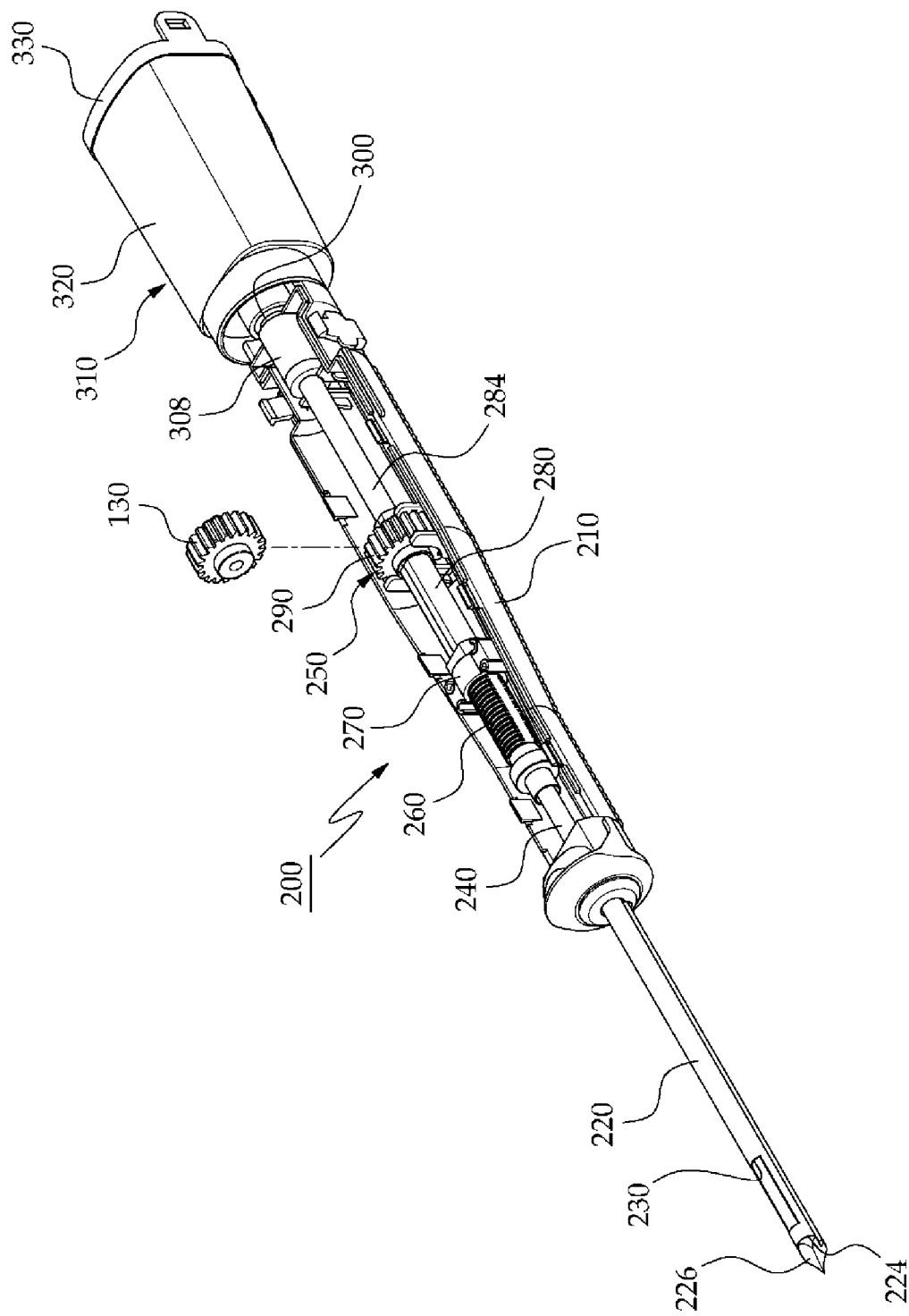
FIG. 3 is a perspective view illustrating the configuration of the probe unit of the biopsy system according to the present invention.
Figure 4:
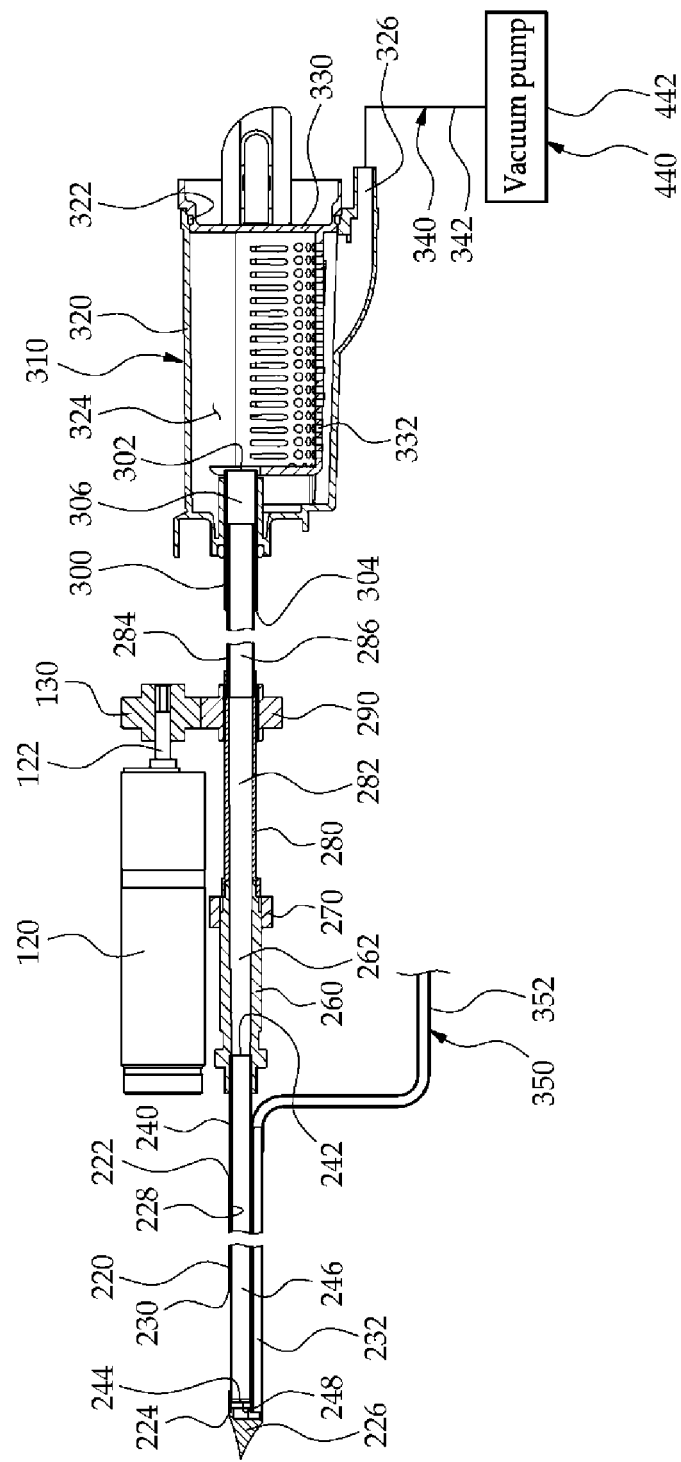
FIG. 4 is a sectional view illustrating the configurations of a needle, a cutter, a drive mechanism, a guide tube and a sample holder of the biopsy system according to the present invention
Figure 5:
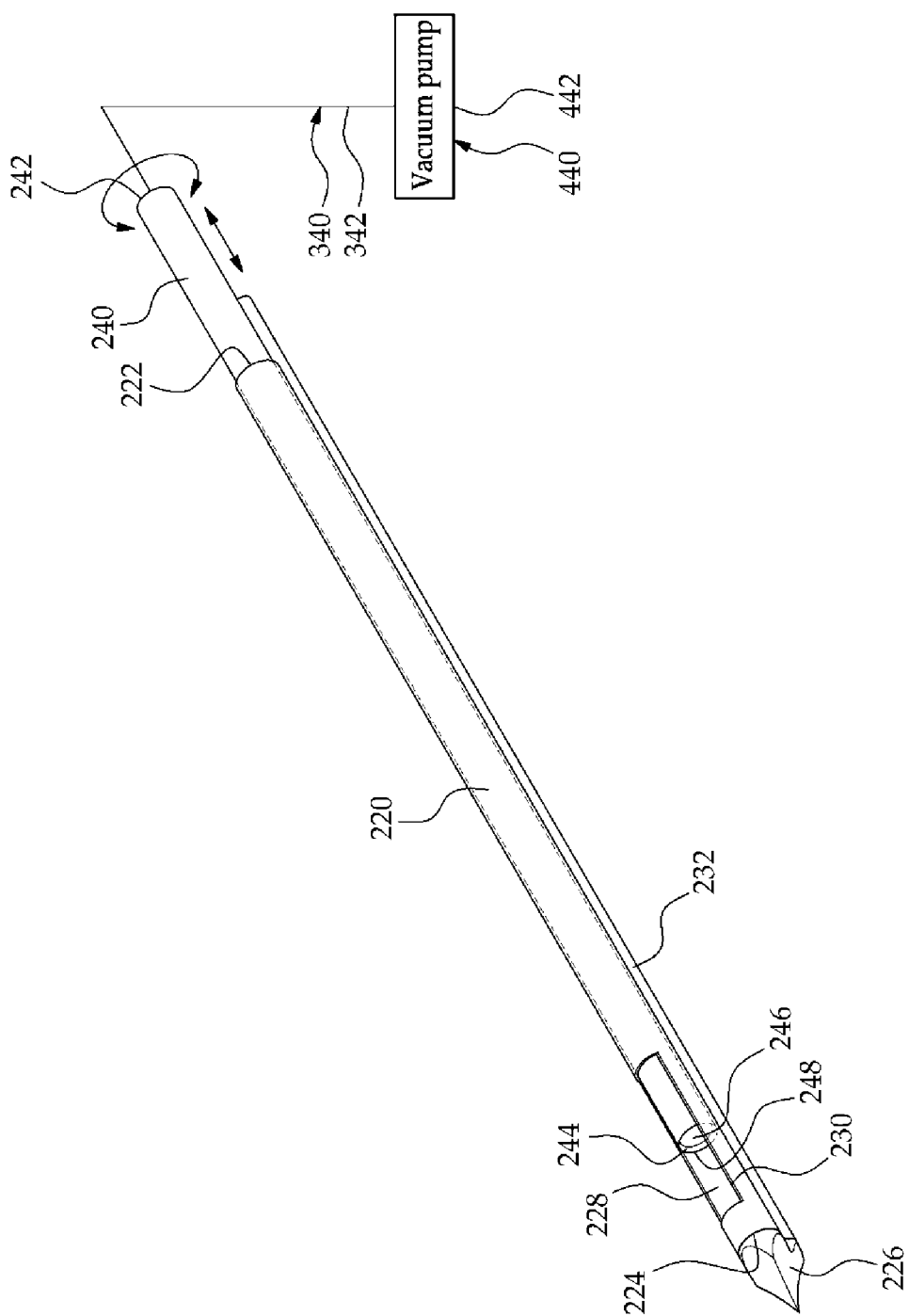
FIG. 5 is a perspective view illustrating the configurations of the needle and the cutter of the biopsy system according to the present invention.

Referring to FIGS. 2 to 4, the probe unit 200 includes a drive mechanism 250 configured to cause the cutter 240 to make rotation and translational movement in conjunction with the driving gear 130. The drive mechanism 250 includes a lead screw 260, a fixed nut 270, a connecting tube 280 and a driven gear 290. The lead screw 260 is mounted within the probe housing 210 so as to make rotation and translational movement and is coupled to the proximal end 242 of the cutter 240. The lead screw 260 is formed of a hollow tube and includes a bore 262 communicating with the passageway 246. The fixed nut 270 is fixedly mounted within the probe housing 210 and is coupled to the lead screw 260 so as to make screw movement together with the lead screw 260. The connecting tube 280 is mounted within the probe housing 210 so as to make rotation and translational movement and is coupled to the lead screw 260.

The connecting tube 280 is formed of a hollow tube and includes a bore 282 communicating with the bore 262 of the lead screw 260. A slide tube 284 is fitted to the bore 282 of the connecting tube 280 so as to extend toward the proximal end 212 of the probe housing 210. The driven gear 290 is mounted within the probe housing 210 so as to make rotation in place and is mounted to an outer surface of the connecting tube 280 so as to rotate the connecting tube 280. The upper portion of the outer surface of the driven gear 290 protrudes from an upper surface of the probe housing 210 and meshes with the driving gear 130.

The probe unit 200 includes a guide tube 300 configured to guide the rotation and translational movement of the connecting tube 280. The guide tube 300 includes a proximal end 302, a distal end 304 and a bore 306. The guide tube 300 is fixedly mounted to the probe housing 210. A fixed block 308 is coupled to an outer surface of the guide tube 300. The fixed block 308 is fixed to the proximal end 312 of the probe housing 210. The proximal end 302 of the guide tube 300 extends out of the probe housing 210. The slide tube 284 is inserted into the bore 306 of the guide tube 300 neighboring the distal end 304 of the slide tube 284 so as to make rotation and translational movement. The bore 306 of the guide tube 300 communicates with the bore 286 of the slide tube 284. The slide tube 284 makes rotation and translational movement while sliding along the bore 306 of the guide tube 300. Similar to the passageway 246 of the cutter 240, each of the bore 262 of the lead screw 260, the bore 282 of the connecting tube 280, the bore 286 of the slide tube 284 and the bore 306 of the guide tube 300 serves as a passageway for transporting a tissue sample 22. In some embodiments, the connecting tube 280 may be removed and the driven gear 290 may be coupled to the lead screw 260. In this case, the lead screw 260 is inserted into the bore 306 of the guide tube 300 so as to make rotation and translational movement. In addition, the slide tube 284 may be removed and the connecting tube 280 may be inserted into the bore 306 of the guide tube 300 so as to make rotation and translational movement.

Referring to FIGS. 1 to 4, the probe unit 200 includes a sample holder 310 for collecting a tissue sample 22. The sample holder 310 includes a cup 320 and a tray 330. The cup 320 is removably coupled to the proximal end 212 of the probe housing 210 and is made of a transparent plastic so that the interior of the cup 320 can be observed from the outside. The cup 320 includes an interior space 324 having an open end 322, and an air outflow port 326 formed in a lower region of an outer surface of the cup 320 so as to communicate with the interior space 324. The tray 330 is coupled to the interior space 324 of the cup 320 so that the interior space 324 can be opened and closed by the tray 330. The bottom of the tray 330 is formed of a grill 332 capable of filtering a liquid such as blood or the like generated during the collection of the tissue sample 22. The tissue sample 22 is collected on the grill 332 after passing through the bore 306 of the guide tube 300.

A flexible tube 342 is connected to the air outflow port 326 via a vacuum line 340. A flexible tube 352 of an air inflow line 350 includes a first end 354, a second end 356, and a passageway 358 formed so as to interconnect the first end 354 and the second end 356. The first end 354 is connected to the air inflow passageway 232. The second end 356 is exposed to the atmosphere in order to introduce an air.

Referring to FIGS. 8 to 11, the flexible tube 352 includes a deformable valve portion 360 formed on an outer surface of the flexible tube 352 neighboring the second end 356. If an external force is applied, the deformable valve portion 360 is deformed into a flat shape to close the passageway 358. If the external force is eliminated, the deformable valve portion 360 is restored to the original shape to open the passageway 358. The thickness of the deformable valve portion 360 is set smaller than the thickness of the remaining portion of the flexible tube 352 in order to enhance the deformability of the deformable valve portion 360. As illustrated in FIGS. 1 and 2, an air filter 370 is coupled to the second end 356 in order to filter an air. The air inflow line 350 includes the air inflow passageway 232 and the air filter 370.

Figure 12:
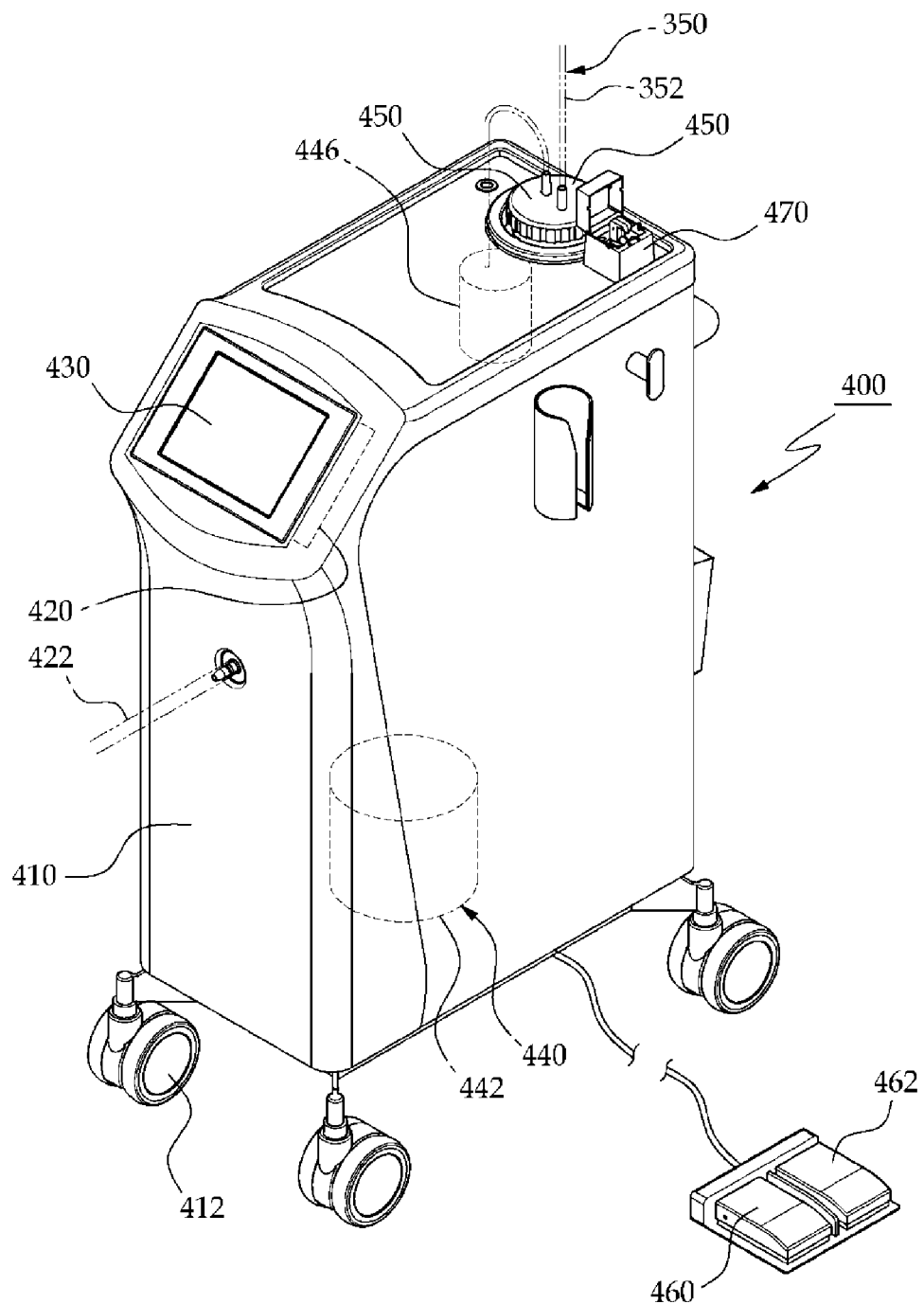
FIG. 12 is a perspective view illustrating the configuration of a control unit of the biopsy system according to the present invention.
Figure 13:
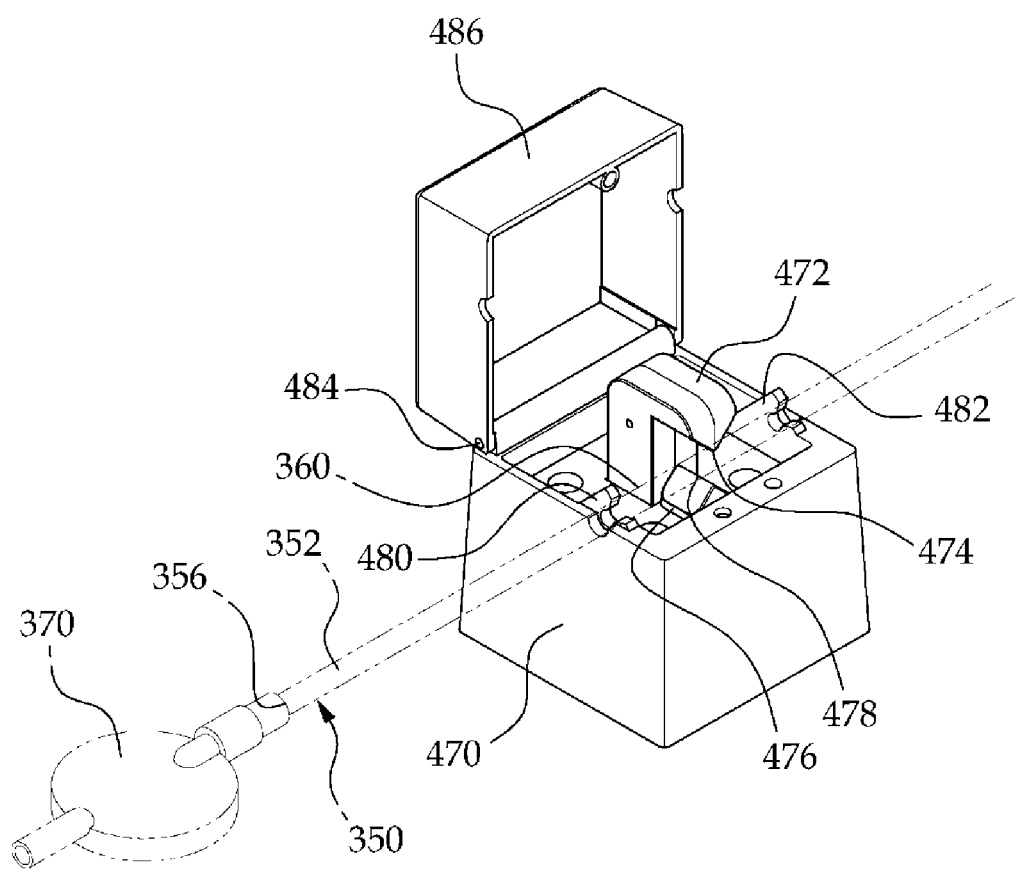
FIG. 13 is a perspective view illustrating the configuration of a solenoid actuator of the biopsy system according to the present invention.
Figure 14:
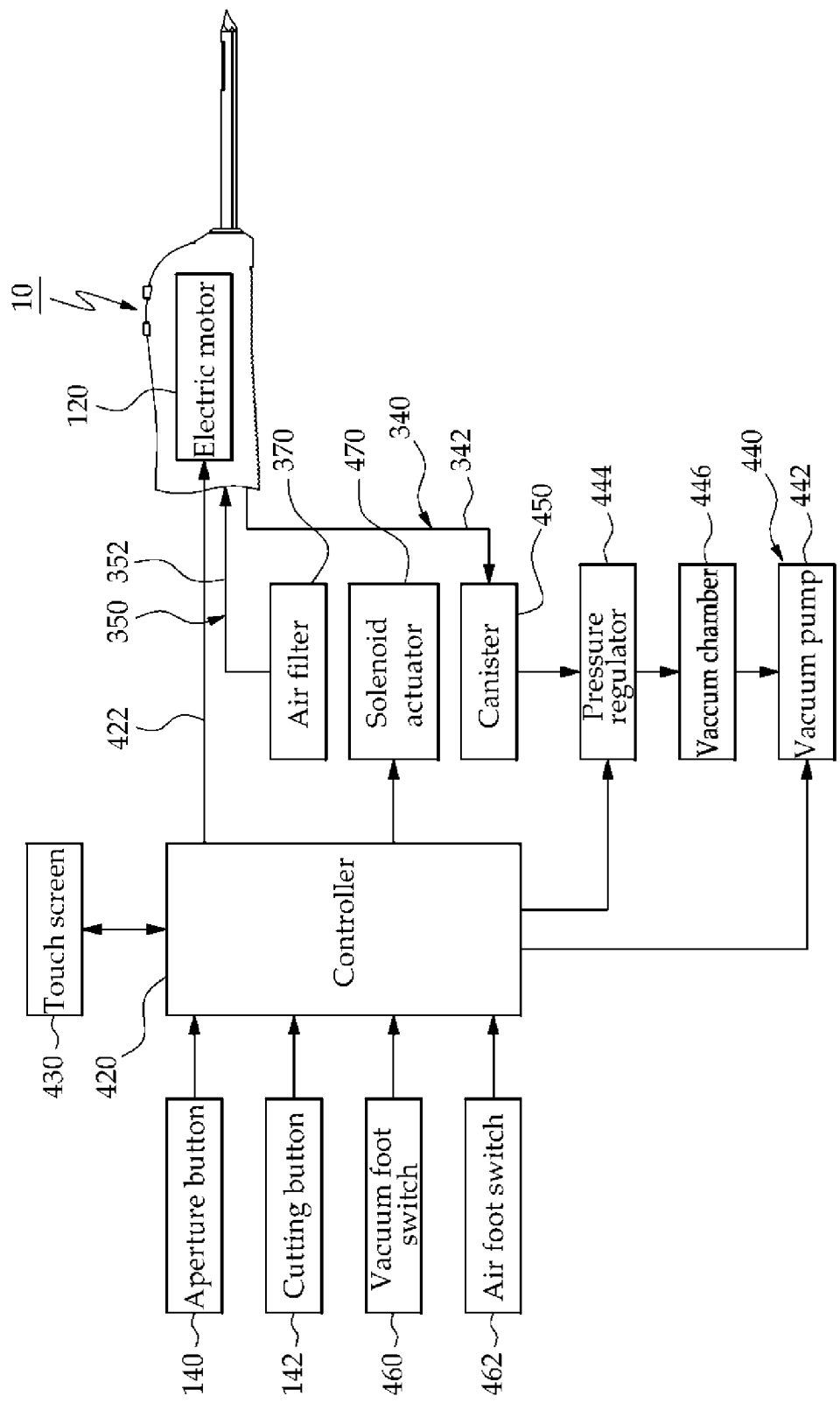
FIG. 14 is a block diagram illustrating the control of the biopsy system according to the present invention.

Referring to FIGS. 12 to 14, the biopsy system 10 according to the present invention includes a control unit 400 for controlling the operations of the drive unit 100 and the probe unit 200. The control unit 400 includes a case 410, a controller 420, a touch screen 430, a vacuum source 440, a canister 450, a vacuum foot switch 460, an air foot switch 462 and a solenoid actuator 470. The case 410 is movable by a plurality of casters 412. The controller 420 and the vacuum source 440 are mounted inside the case 410. The controller 420 is connected to the electric motor 120, the aperture button 140 and the cutting button 142 via a cable 422. The touch screen 430 is mounted to an upper surface of the case 410 so that the touch screen 430 can be easily operated by a user. The vacuum source 440 includes a vacuum pump 442, a pressure regulator 444 and a vacuum chamber 446. The canister 450 is removably coupled to an upper surface of the case 410. The vacuum pump 442 is connected by a flexible hose 342 to the air outflow port 326 via the pressure regulator 444, the vacuum chamber 446 and the canister 450.

The controller 420 controls the operations of the electric motor 120, the vacuum pump 442 and the solenoid actuator 470 in response to signals inputted from the aperture button 140, the cutting button 142, the touch screen 430, the vacuum foot switch 460 and the air foot switch 462. The touch screen 430 may be formed of a liquid crystal display which displays the operation of the biopsy system 10. A user may control the operation of the vacuum pump 442 by operating the vacuum foot switch 460. A user may control the operation of the solenoid actuator 470 by operating the air foot switch 462.

The solenoid actuator 470 is mounted to an upper surface of the case 410. The solenoid actuator 470 includes a first push rod 472 capable of opening and closing the deformable valve portion 360. A wedge tip 474 is formed at a distal end of the first push rod 472 so as to press the deformable valve portion 360 by making line contact therewith. The solenoid actuator 470 includes a second push rod 476 which faces the first push rod 472 so as to support the deformable valve portion 360. A wedge tip 478 is formed in an upper portion of the second push rod 476 so that the wedge tip 478 forms a pair with the wedge tip 474 to press the deformable valve portion 360. In another embodiment, the second push rod 476 may be formed of a support block which supports the deformable valve portion 360.

As clearly illustrated in FIG. 13, a pair of hooks 480 and 482 is disposed at the opposite sides of the second push rod 476 in a mutually-aligned relationship in order to fix the flexible tube 352. When the flexible tube 352 is brought into engagement with the hooks 480 and 482, the deformable valve portion 360 is placed on the second push rod 476. In some embodiments, the second end 356 of the flexible tube 352 may be connected to a solenoid valve which interrupts a flow of an air. The flexible tube 352 may be fixed by a clamp so that the flexible tube 352 passes through the second push rod 476. The solenoid actuator 470 includes a cover 486 which is rotated about a hinge 484 to cover the first push rod 472, the second push rod 476 and the hooks 480 and 482.

Hereinafter, descriptions will be made on the operation of the biopsy device and system according to the present invention configured as above.

Referring to FIGS. 4, 8, 13 and 14, the cutter 240 closes the sample receiving port 230 of the needle 220. The flexible tube 350 is brought into engagement with the hooks 480 and 482 so that the deformable valve portion 360 is placed on the wedge tip 478 of the second push rod 476. By the operation of the solenoid actuator 470, the first and second push rods 472 and 476 are moved forward to press the deformable valve portion 360. The wedge tips 474 and 478 of the first and second push rods 472 and 476 press the deformable valve portion 360 by line contact, eventually closing the passageway 358. In a state in which the sample receiving port 230 is closed, a user sticks the needle 220 into the tissue 20 of a legion of a patent so that the sample receiving port 230 reaches the legion.

Referring to FIGS. 4, 9, 12 and 14, if a user operates the aperture button 140, the electric motor 120 rotates in one direction, for example, clockwise. The drive power of the electric motor 120 is delivered to the connecting tube 280 via the driving gear 130 and the driven gear 290, whereby the connecting tube 280, the lead screw 260 and the cutter 240 rotate together at the same speed. Furthermore, the lead screw 260 is translation-moved from the distal end 214 of the probe housing 210 toward the proximal end 212 thereof by the screw movement with the fixed nut 270. The cutter 240, the connecting tube 280 and the slide tube 284 make translational movement together with the lead screw 260. The cutter 240 is moved backward, whereby the sample receiving port 230 closed by the cutter 240 is opened.

Figure 9:
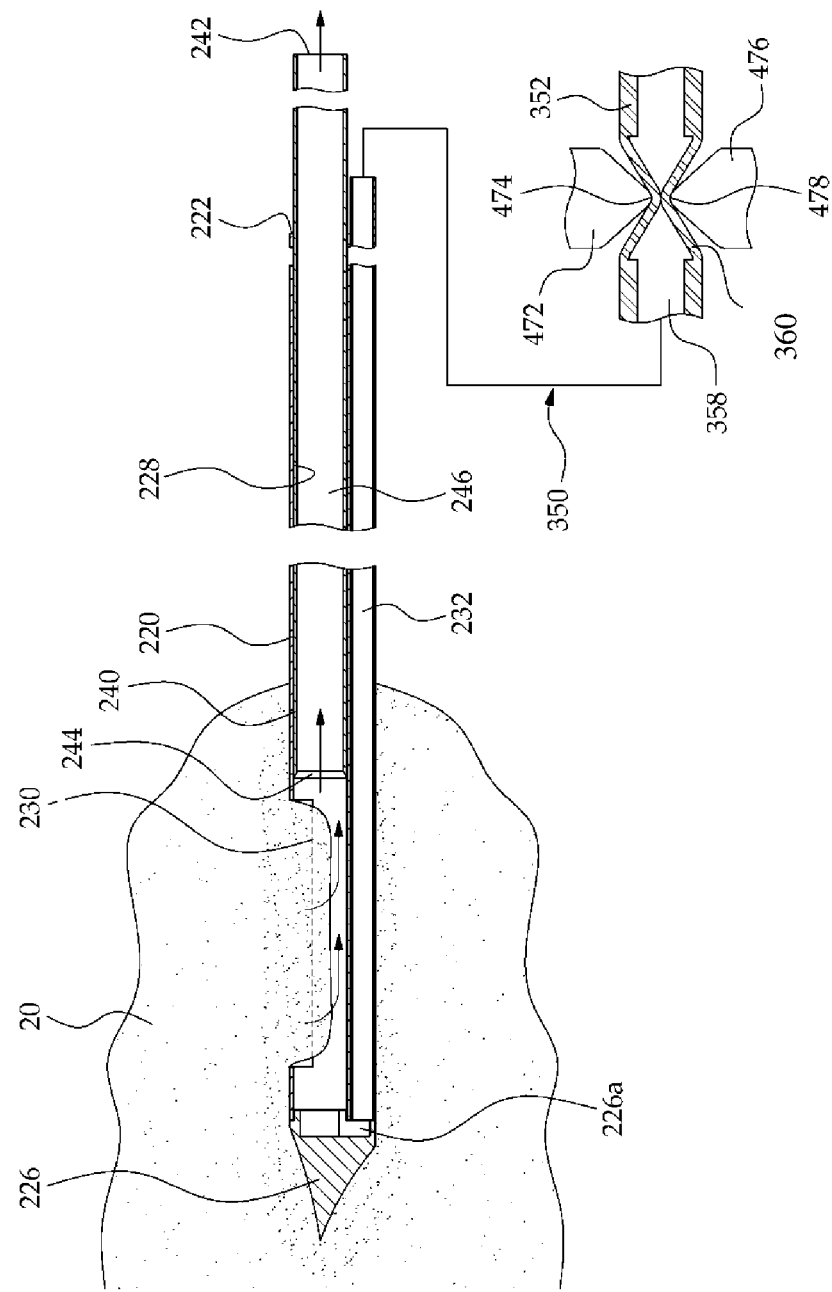
FIG. 9 is a sectional view illustrating an operation of sucking the tissue into a passageway of the needle in FIG. 8.

As illustrated in FIG. 9, the collection amount of the tissue sample 22 is set depending on the aperture ratio of the sample receiving port 230. If a user operates the vacuum foot switch 460 after the sample receiving port 230 is opened, the vacuum pump 442 is operated to generate an air suction force. The tissue 20 existing around the sample receiving port 230 is introduced into the passageway 228 through the sample receiving port 230 by the air suction force.

Figure 10:
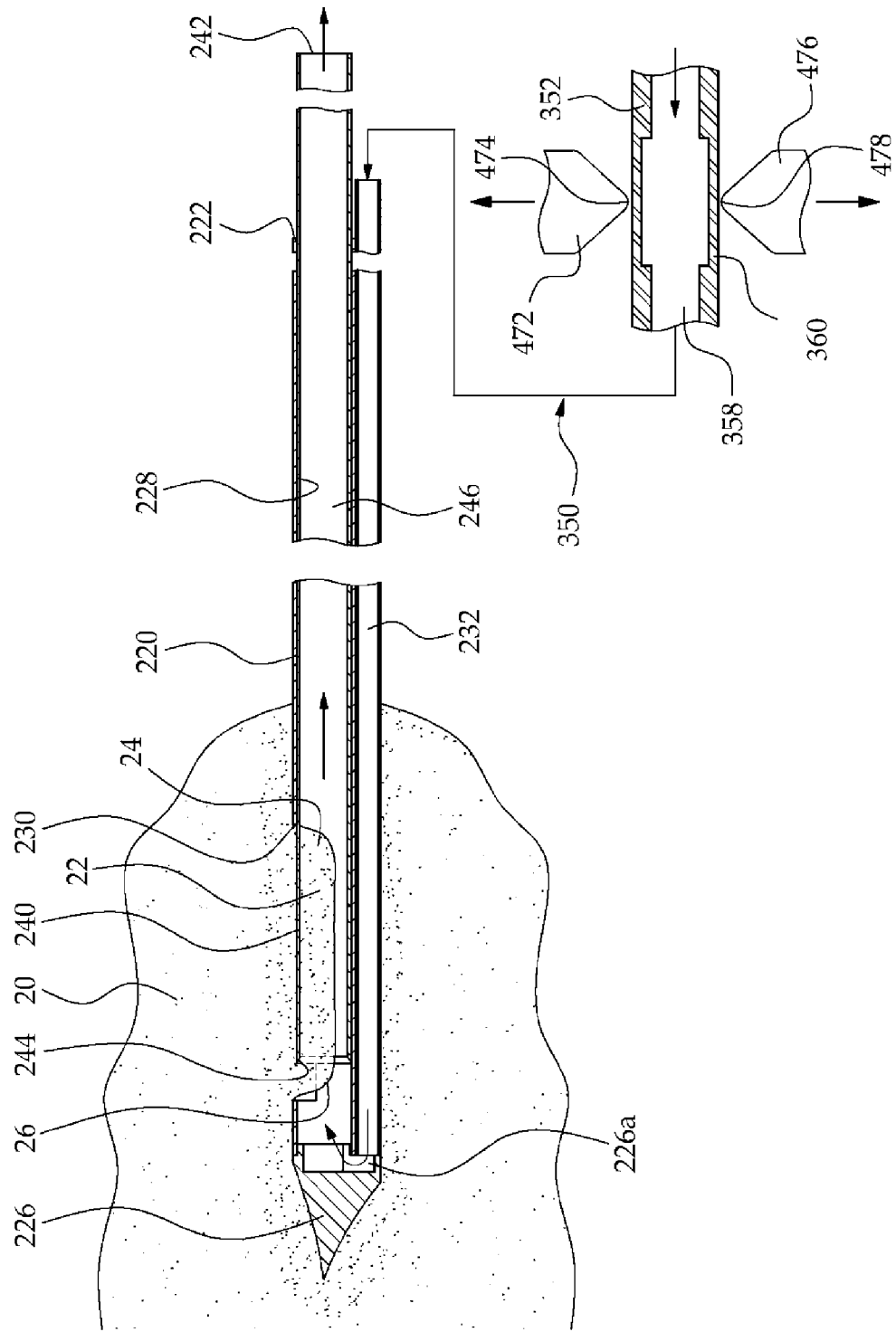
FIG. 10 is a sectional view illustrating an operation of creating an atmospheric pressure within the passageway of the needle prior to the cutting completion time of a tissue sample in FIG. 9.
Figure 11:
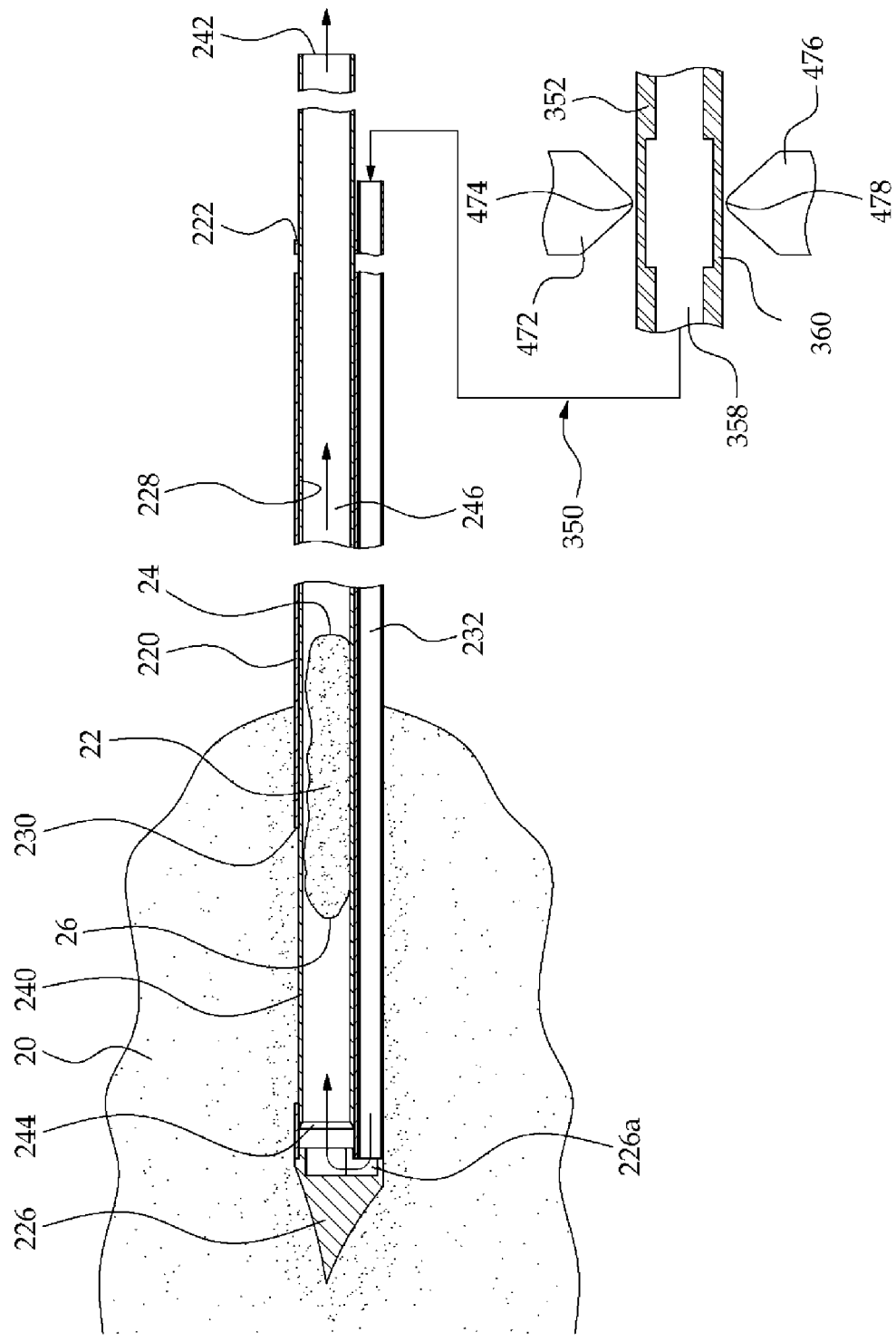
FIG. 11 is a sectional view illustrating an operation of transporting a tissue sample through a passageway of the cutter.

Referring to FIGS. 10 and 11, if a user operates the cutting button 142, the electric motor 120 rotates counterclockwise. By the operation of the electric motor 120, the connecting tube 280, the lead screw 260 and the cutter 240 rotate together at the same speed and make translational movement from the proximal end 212 of the probe housing 210 toward the distal end 214 thereof. Furthermore, the slide tube 284 makes translational movement while sliding along the bore 306 of the guide tube 300. At this time, the slide tube 284 is not removed out of the distal end 304 of the guide tube 300. Accordingly, the cutter 240, the lead screw 260, the connecting tube 280 and the slide tube 284 may make rotation and translational movement at the same speed. By the rotation and translational movement of the cutter 240, the blade edge 248 cuts the tissue 20 introduced into the passageway 228 and collects the tissue sample 22. If the cutting of the tissue 20 is completed and if the sample receiving port 230 is closed by the cutter 240, the electric motor 120 is stopped.

In the meantime, if a user operates the air foot switch 462 before the sample receiving port 230 is closed, namely before the cutting completion time at which the tissue sample 22 is completely cut by the cutter 240, the solenoid actuator 470 is operated to move the first and second push rods 472 and 476 backward. If the first and second push rods 472 and 476 are moved backward, the deformable valve portion 360 pressed by the first and second push rods 472 and 476 is restored to the original position, thereby opening the passageway 358. Preferably, the creation of the atmospheric pressure by the operation of the solenoid actuator 470 may be performed immediately before the cutting completion time of the tissue sample 22.

Subsequently, if the passageway 358 is opened, an air is filtered while passing through the air filter 370 and is then introduced into the passageway 228 neighboring the tip 226 via the passageway 358 and the air inflow passageway 232, thereby creating the atmospheric pressure. If the atmospheric pressure is created within the passageway 228 around the tip 226, a pressure difference between the transport-direction front end 24 and the transport-direction rear end 26 of the tissue sample 22 grows larger. That is to say, the interior of the passageway 228 neighboring the transport-direction front end 24 of the tissue sample 22 is kept at a vacuum pressure by the suction force of the vacuum pump 442. The interior of the passageway 228 neighboring the transport-direction rear end 26 of the tissue sample 22 is kept at an atmospheric pressure by the flow of an air. If a pressure difference between the transport-direction front end 24 and the transport-direction rear end 26 of the tissue sample 22 is instantaneously generated in this way, the transport of the tissue sample 22 is smoothly performed due to the pressure difference. Furthermore, the atmospheric pressure is created within the passageway 228 before the sample receiving port 230 is closed by the cutter 240, namely before the blade edge 248 of the cutter 240 passes through the inner end of the sample receiving port 230 neighboring the distal end 224 of the needle 220. This facilitates the cutting and transport of the tissue sample 22. In some embodiments, the time of creation of the atmospheric pressure may be set to range from the time at which the sample receiving port 230 is half-closed by the cutter 240 to the time at which the sample receiving port 230 is completely closed by the cutter 240.

In the meantime, the tissue sample 22 is transported from the distal end 224 of the needle 220 toward the proximal end 242 of the cutter 240 by the suction force of the vacuum pump 442. The tissue sample 22 is transported through the passageway 228 of the needle 220, the passageway 246 of the cutter 240, the bore 262 of the lead screw 260, the bore 282 of the connecting tube 280, the bore 286 of the slide tube 284 and the bore 306 of the guide tube 300 and is discharged to the tray 330. The liquid such as blood or the like generated during the collection of the tissue sample 22 is filtered by the grill 332 and is fed to the canister 450 via the flexible tube 342.

The embodiments described above are nothing more than preferred embodiments of the present invention and are not intended to limit the scope of the present invention. Those skilled in the art may make different changes, modifications or substitutions without departing from the spirit and scope of the present invention. It is to be understood that such changes, modifications or substitutions fall within the scope of the present invention.

DESCRIPTION OF REFERENCE NUMERALS

20: tissue, 22: tissue sample, 100: drive unit, 110: drive housing, 120: electric motor, 130: driving gear, 200: probe unit, 210: probe housing, 220: needle, 228: passageway, 230: sample receiving port, 232: air inflow passageway, 240: cutter, 246: passageway, 250: drive mechanism, 260: lead screw, 270: fixed nut, 280: connecting tube, 290: driven gear, 300: guide tube, 310: sample holder, 320: cup, 330: tray, 340: vacuum line, 342: flexible tube, 350: air inflow line, 352: flexible tube, 360: deformable valve portion, 370: air filter, 400: control unit, 410: case, 420: controller, 440: vacuum source, 442: vacuum pump, 450: canister, 470: solenoid actuator, 472: first push rod, 476: second push rod, 480 or 482: hook, 486: cover

What is claimed is:

1. A biopsy device for cutting tissue and collecting a tissue sample, comprising:

a needle including a proximal end blocked by a tip, a distal end, a passageway and a sample receiving port configured to introduce the tissue and formed on an outer surface of the needle neighboring the distal end so as to communicate with the passageway;

a cutter disposed in the passageway of the needle so as to make rotation and translational movement, the cutter including a proximal end disposed within the passageway of the needle, a distal end disposed outside the passageway of the needle and a passageway communicating with the passageway of the needle;

a drive mechanism configured to cause the cutter to make rotation and translational movement, the drive mechanism including an electric motor configured to provide drive power for causing the cutter to make rotation and translational movement, a driving gear connected to the electric motor so that the driving gear is rotated by the electric motor, a lead screw coupled to the proximal end of the cutter so as to make rotation and translational movement together with the cutter and provided with a bore communicating with the passageway of the cutter, a fixed nut coupled to the lead screw so as to make screw movement together with the lead screw and fixed so as to cause the lead screw to make translational movement, a connecting tube coupled to the lead screw so as to make rotation and translational movement together with the lead screw and provided with a bore communicating with the bore of the lead screw, a driven gear mounted to an outer surface of the connecting tube so as to mesh with the driving gear, a guide tube provided with a bore into which the connecting tube is inserted so as to make rotation and translational movement, and a slide tube coupled to the connecting tube so as to extend from the connecting tube and inserted into the bore of the guide tube so as to make rotation and translational movement;

a vacuum line configured to be connected to a vacuum pump and the passageway of the cutter so as to suck the tissue introduced into the passageway of the needle through the sample receiving port;

an air inflow line interconnecting the passageway of the needle and the atmosphere existing outside the needle, without connecting to a compressed air source or a liquid source, the air inflow line including an air inflow passageway formed along a longitudinal direction of the needle so as to be partitioned from the passageway of the needle and kept in communication with the passageway of the needle neighboring the distal end of the needle, and a flexible tube, wherein the flexible tube of the air inflow line includes a first end, a second end, and a passageway interconnecting the first end and the second end, wherein the first end is connected to the air inflow passageway, and the second end is exposed to the atmosphere so as to introduce air directly from the atmosphere, wherein the flexible tube of the air inflow line further includes a deformable valve portion neighboring the second end, and an air filter coupled to the second end in order to filter the air introduced from the atmosphere, wherein a thickness of the deformable valve portion is smaller than that of the remaining portion of the flexible tube of the air inflow line; and a solenoid actuator including a first push rod and a second push rod facing the first push rod, wherein each of the first push rod and the second push rod has a wedge tip, wherein the deformable valve portion of the flexible tube is placed between the first push rod and second push rod so that the wedge tips of the first push rod and the second push rod press and release the deformable valve portion of the flexible tube so as to open and close the passageway of the flexible tube of the air inflow line, and wherein the solenoid actuator is configured to open the passageway of the flexible tube of the air inflow line by releasing the flexible tube before the sample receiving port is closed by the cutter.

2. The device of claim 1, wherein a connection passageway is formed on an inner surface of the tip so as to interconnect the passageway of the needle and the air inflow passageway.

3. The device of claim 1, wherein the solenoid actuator further includes: a pair of hooks disposed at the opposite sides of the second push rod in a mutually-aligned relationship so as to fix the flexible tube.

\* \* \* \* \*